(12) United States Patent
Iwai (10) Patent No.: US 10,512,709 B2
(45) Date of Patent: Dec. 24, 2019

(54) POROUS COMPOSITE AND BONE REGENERATION MATERIAL

(71) Applicant: TOYOBO CO., LTD., Osaka-shi, Osaka (JP)

(72) Inventor: Atsushi Iwai, Otsu (JP)

(73) Assignee: TOYOBO CO., LTD., Osaka (JP)

( * ) Notice: Subject to any disclaimer, the term of this patent is extended or adjusted under 35 U.S.C. 154(b) by 0 days.

(21) Appl. No.: 15/757,705

(22) PCT Filed: Sep. 7, 2016

(86) PCT No.: PCT/JP2016/076227
§ 371 (c)(1),
(2) Date: Mar. 6, 2018

(87) PCT Pub. No.: WO2017/043498
PCT Pub. Date: Mar. 16, 2017

(65) Prior Publication Data
US 2019/0038801 A1     Feb. 7, 2019

(30) Foreign Application Priority Data

Sep. 8, 2015   (JP) ................................ 2015-176454
Sep. 8, 2015   (JP) ................................ 2015-176455

(51) Int. Cl.
*A61L 27/12* (2006.01)
*A61L 27/56* (2006.01)
*A61L 27/42* (2006.01)
*A61L 27/24* (2006.01)

(52) U.S. Cl.
CPC .............. *A61L 27/12* (2013.01); *A61L 27/24* (2013.01); *A61L 27/425* (2013.01); *A61L 27/56* (2013.01); *A61L 2400/08* (2013.01); *A61L 2430/02* (2013.01)

(58) Field of Classification Search
CPC .. A61L 27/46; A61L 2400/08; A61L 2430/02; A61L 27/00; A61L 27/12; A61L 27/24; A61L 27/425; A61L 27/56; C08L 89/06
See application file for complete search history.

(56) References Cited

U.S. PATENT DOCUMENTS

| 4,888,366 | A  | 12/1989 | Chu et al. |
| 2005/0042252 | A1 | 2/2005 | Tanaka et al. |
| 2007/0172033 | A1 | 7/2007 | Gorges et al. |
| 2008/0234396 | A1 | 9/2008 | Shoji et al. |
| 2009/0149634 | A1 | 6/2009 | Shoji et al. |

FOREIGN PATENT DOCUMENTS

| JP | 1-158964 A | 6/1989 |
| JP | 6-70113 A | 3/1993 |
| JP | 2003-260124 A | 9/2003 |
| JP | 2005-279078 A | 10/2005 |
| JP | 2006-167445 A | 6/2006 |
| JP | 2009-132601 A | 6/2009 |
| JP | 2010-504817 A | 2/2010 |
| JP | 2010-273847 A | 12/2010 |
| JP | 2015-54055 A | 3/2015 |
| WO | 2008/042108 A1 | 4/2008 |
| WO | 2016/084413 A1 | 6/2016 |
| WO | 2016/163396 A1 | 10/2016 |

OTHER PUBLICATIONS

Kamakura, S. et al., "Octacalcium Phosphate Combined with Collagen Orthotopically Enhances Bone Regeneration", Journal of Biomedical Materials Research Part B: Applied Biomaterials, Nov. 1, 2006, vol. 79B, No. 2, pp. 210-217; cited in Extended (supplementary) European Search Report dated Jul. 20, 2018.

Toyobo, "Clinical Trials of Induced Bone Regeneration Devices to Begin—Aiming for Commercialization as a Next-Generation Bone Reconstruction Material-", Apr. 13, 2015; cited in Extended (supplementary) European Search Report dated Jul. 20, 2018. (3 pages).

Assender, H. et al., "How Surface Topography Relates to Materials' Properties", Science, Aug. 9, 2002, pp. 973-976; cited in Extended (supplementary) European Search Report dated Jul. 20, 2018.

Extended (supplementary) European Search Report dated Jul. 20, 2018, issued in counterpart European Application No. 16844359.6. (11 pages).

Kawai et al., "Reconstruction of Critical-Sized Bone Defect in Dog Skull by Octacalcium Phosphate Combined with Collagen", Clinical Implant Dentistry and Related Research, 2011, vol. 13, No. 2, pp. 112-123, cited in the specification. (12 pages).

Kawai et al., "First Clinical Application of Octacalcium Phosphate Collagen Composite in Human Bone Defect", Tissue Engineering Part A, 2014, vol. 20, Nos. 7 and 8, pp. 1336-1341, cited in ISR, the specification and the Office Actions dated Nov. 18, 2015 for the corresponding JP patent application No. 2015-176454 and No. 2015-176455. (6 pages).

(Continued)

*Primary Examiner* — Robert A Wax
*Assistant Examiner* — Olga V. Tcherkasskaya
(74) *Attorney, Agent, or Firm* — Westerman, Hattori, Daniels & Adrian, LLP (57) ABSTRACT

[Problem to be Solved] To provide a porous composite that has excellent uniform dispersability of OCP and that comprises OCP and collagen in a sufficiently mixed state; and a bone regeneration material comprising the porous composite. [Means for Solution] A porous composite comprising octacalcium phosphate and collagen, characterized in that in an image obtained by enlarging a 5.0-mm×5.0-mm range of a plane of the porous composite 15 times with a scanning electron microscope (SEM), agglomerated particles of octacalcium phosphate have a fractal dimension (D) of 0.70 or more; and the area of c) portions consisting of collagen accounts for 5% or less of the total area of a) portions consisting of agglomerated particles of octacalcium phosphate, b) portions consisting of octacalcium phosphate microparticles and collagen, and the c) portions consisting of collagen.

8 Claims, 4 Drawing Sheets

(56) References Cited

OTHER PUBLICATIONS

Kawai et al., "Synthetic Octacalcium Phosphate Augments Bone Regeneration Correlated with its Content in Collagen Scaffold", Tissue Engineering Part A, 2009, vol. 15, No. 1, pp. 23-32, cited in the specification. (12 pages).
Legeros, "Preparation of Octacalcium Phosphate (OCP): A Direct Fast Method", Calcified Tissue International, 1985, vol. 37, pp. 194-197, cited in the specification. (4 pages).
International Search Report dated Oct. 11, 2016, issued in counterpart application No. PCT/JP2016/076227. (1 page).

POROUS COMPOSITE AND BONE REGENERATION MATERIAL

TECHNICAL FIELD

The present invention relates to a porous composite and a bone regeneration material comprising the porous composite.

BACKGROUND ART

As conventionally used bone regeneration materials, calcium phosphates, such as hydroxyapatite (HA), are known (see, for example, JP2010-273847A, JP2003-260124A, JP2009-132601A and JP2005-279078A).

In recent years, octacalcium phosphate (hereinafter referred to as "OCP"), which is a precursor of HA, has been found to have high action of promoting bone regeneration and high absorbability in vivo, compared with other calcium phosphates, such as HA and β-tricalcium phosphate (β-TCP) (see, for example, JP2006-167445A). Thus, OCP has particularly excellent properties as a bone regeneration material among calcium phosphates.

However, OCP, which is an inorganic substance, has poor shape-imparting properties. Therefore, applying OCP alone so as to, for example, regenerate an extensive bone defect region is difficult. In light of this difficulty, using a composite of OCP and collagen as a bone regeneration material has been proposed (see, for example, JP2006-167445A).

Clinical Implant Dentistry and Related Research, Vol. 13, No. 2, pages 112 to 123, 2011 and Tissue Engineering Part A, Vol. 20, Nos. 7 to 8, pages 1336 to 1341, 2014 disclose that a composite of OCP and collagen is useful as a bone regeneration material in dogs and humans, respectively. In the study of the composite of OCP and collagen as a bone regeneration material, only OCP particles having a particle size of 300 μm to 500 μm were used.

Tissue Engineering Part A, Vol., 15, No. 1, pages 23 to 32, 2009 discloses a comparison of an in vivo-implanted composite of OCP and collagen and an in vivo-implanted porous material consisting only of collagen in terms of bone regeneration. Tissue Engineering Part A, Vol., 15, No. 1, pages 23 to 32, 2009 discloses that a porous material consisting only of collagen does not bring about sufficient bone regeneration.

SUMMARY OF INVENTION

Technical Problem

When implanted in vivo, OCP is known to convert to a bioanalogue hydroxyapatite and have excellent osteoconduction, i.e., promote bone formation by activating osteoblasts present in bone tissue. It has been reported that the implanted OCP itself actually has bioabsorbability in vivo and promotes bone regeneration. It has also been reported that OCP has a higher ability to promote differentiation of osteoblasts from preosteoblasts than HA. In a bone regeneration material comprising a composite of OCP and collagen as well, OCP exhibits bioabsorbability and has an excellent ability to promote bone regeneration and osteoblast differentiation as described above. However, bone regeneration takes a relatively long period of time, i.e., several weeks to several months, although it may vary depending on the site, size, shape, etc., of the bone defect. To exhibit long-term osteoconduction, it is considered to be important to impart sustained effect properties to OCP.

In porous composites comprising OCP and collagen, no analysis that focuses on the relationship between agglomerated particles of OCP and uniform dispersion has been heretofore performed. Accordingly, an object of the present invention is to provide a porous composite comprising OCP and collagen, in which OCP is uniformly dispersed while OCP is maintained as large agglomerated particles. Another object is to provide a bone regeneration material comprising the porous composite.

Solution to Problem

In view of the above problem, the present inventors carried out extensive research and found that a porous composite that has excellent uniform dispersibility of OCP and that comprises OCP and collagen in a sufficiently mixed state can be obtained by controlling the level of stirring within a specific range when a mixing step of OCP and collagen is performed in the process of producing a porous composite comprising OCP and collagen. As a result of further research and improvement, the present, inventors provide inventions represented by the following.

[1] A porous composite comprising octacalcium phosphate and collagen, characterized in that in an image obtained by enlarging a 5.0-mm×5.0-mm range of a plane of the porous composite 15 times with a scanning electron microscope (SEM), agglomerated particles of octacalcium phosphate have a fractal dimension (D) of 0.70 or more; and the area of c) portions consisting of collagen accounts for 5% or less of the total area of a) portions consisting of agglomerated particles of octacalcium phosphate, b) portions consisting of octacalcium phosphate microparticles and collagen, and the c) portions consisting of collagen.

[2] A porous composite comprising octacalcium phosphate and collagen, characterized in that in an image obtained by enlarging a 5.0-mm×5.0-mm range of a plane of the porous composite 15 times with a scanning electron microscope (SEM), agglomerated particles of octacalcium phosphate have a fractal dimension (D) of 0.60 or more;

the area of agglomerated particles of octacalcium phosphate having a length of 300 μm or more accounts for 75% or more of the total area of the agglomerated particles of octacalcium phosphate; and the area of c) portions consisting of collagen accounts for 5% or less of the total area of a) portions consisting of agglomerated particles of octacalcium phosphate, b) portions consisting of octacalcium phosphate microparticles and collagen, and c) the portions consisting of collagen.

[3] The porous composite according to [1] or [2], wherein the porous composite has a compressive modulus of 0.08 MPa or more.

[4] A bone regeneration material comprising the porous composite according to any one of [1] to [3].

Advantageous Effects of Invention

According to the present invention, agglomerated particles of OCP, which have a large particle size, and OCP microparticles are uniformly dispersed. This can prevent fluctuations in osteoconduction derived from non-uniformity of the porous composite, and OCP can be expected to exert an excellent effect of promoting bone regeneration over a prolonged period of time. Furthermore, due to the uniform dispersion of OCP, the obtained porous composite can have a higher compressive modulus (Young's modulus).

Therefore, a porous composite can be provided that has excellent processability and that is less likely to be damaged. A bone regeneration material comprising the porous composite can also be provided.

DESCRIPTION OF EMBODIMENTS

Porous Composite

The porous composite of the present invention is a porous composite comprising OCP and collagen (an OCP/collagen composite). A preferred embodiment of the porous composite of the present invention is a porous composite in which collagen has a three-dimensional sponge-like structure and fine particles of OCP are present in the sponge-like structure, while agglomerate particles of OCP having a size of at least 100 μm or more are present. The bone regeneration material comprising the porous composite of the present invention, which has a porous structure, allows osteoblasts to migrate into the porous composite, thus forming an internal bone that promotes new bone formation.

OCP ($Ca_8H_2(PO_4)_6 \cdot 5H_2O$) can be prepared by various known methods. For example, OCP can be prepared by the drop method of LeGeros (LeGeros R.Z., Calcif Tissue Int 37: 194-197, 1985) or the method using a synthesizing apparatus (three-way pipe) disclosed in JPH5-070113A. Alternatively, OCP can be prepared by a mixing method. Specifically, OCP can be obtained, for example, by mixing an aqueous sodium dihydrogen phosphate solution and an aqueous calcium acetate solution under appropriate conditions and collecting the generated precipitate. Preferably, the OCP obtained from the precipitate is dried, pulverized using an electric mill or the like, and used in the form of a particulate powder. The particle size is preferably in the range of 10 μm to 1000 μm, more preferably 100 μm to 500 μm and even more preferably 300 μm to 500 μm. The particle size can be classified, for example, by sieving based on the size of the sieve openings.

The source, properties, etc., of the collagen are not particularly limited. Various collagens can be used. Preferably used is enzyme-solubilized collagen that is obtained by solubilizing collagen with a protease (e.g., pepsin or pronase) and from which telopeptides have been removed. The type of collagen is preferably type-I, type-II, type-III, or type-IV collagen, which are fibrous collagens. Type-I collagen, which is abundant in vivo, or a mixture of type-I collagen and type-III collagen, is particularly preferable. The raw material of the collagen is not particularly limited. Collagen derived from the skin, bone, tendon, or the like of pigs or cows, the scales of fish, etc., can be preferably used. Collagen, which is an organism-derived component, has a feature of high safety. In particular, enzyme-solubilized collagen is also less allergenic and is thus particularly preferable. Commercially available collagen can also be used.

The mixing ratio of OCP to collagen in the porous composite of the present invention can be appropriately adjusted according to the desired shape-imparting properties, operability, biocompatibility, etc. For example, the mixing ratio of calcium phosphate to 1 part by weight of collagen is preferably 0.5 parts by weight to 35 parts by weight, more preferably 1 part by weight to 20 parts by weight, and even more preferably 2 parts by weight to 10 parts by weight. If the amount of OCP is less than 0.5 parts by weight per part by weight of collagen, the obtained composite may have a poor bone regeneration function. If the amount of OCP is more than 35 parts by weight, poor shape-imparting properties may result.

A feature of the porous composite of the present invention is that in an image obtained by enlarging a 5.0-mm×5.0-mm range of a plane of the porous composite 15 times with a scanning electron microscope (SEM), agglomerated particles of OCP have a fractal dimension (D) of 0.60 or more. The fractal dimension (D) is preferably 0.70 or more, and more preferably 0.80 or more. A larger fractal dimension (D) indicates a better dispersed state of agglomerated particles of OCP.

When the fractal dimension (D) is less than 0.60, uniform osteoconduction may not occur at the site to which the porous composite is applied. Furthermore, a sustained effect of OCP may not be expectable. In particular, to continuously promote osteoconduction over a period of several weeks to several months required for bone regeneration, the uniform presence of large agglomerated particles, which prevents OCP from disappearing soon, is considered to be important. OCP also functions to reinforce the strength of the skeletal structure of collagen in the porous composite. As described below, a lower fractal dimension of agglomerated particles of OCP reduces the compressive modulus. A low compressive modulus results in less operating ease in filling a bone defect site. When a bone defect site is filled with the porous composite of the present invention, a collapse of the porous composite or a crushing of pores, if it occurred, would adversely affect the subsequent bone regeneration. Specifically, the fractal dimension (D) is calculated in the following manner.

SEM Image of Porous Composite

A cross-sectional photograph of the porous composite is taken with a scanning electron microscope (SEM) in such a manner that the photograph includes at least a 5.0-mm×5.0- mm square range that is a plane of the porous composite. The photographing conditions are as follows:
accelerating voltage: 15.0 kV,
low vacuum (30 Pa),
backscattered electron detection,
working distance (WD): 40 mm,
magnification: ×15.

When the porous composite has a plane of at least 5.0-mm×5.0-mm on its outer surface, the surface can be photographed. The 5.0-mm×5.0-mm plane to be photographed may be a cross-section of the porous composite. In that case, a smooth cut surface of the porous composite can be photographed. The surface to be photographed is preferably a surface with no coating or the like. For example, when the outer surface of the porous composite has a coating, a cross-section obtained by cutting in such a manner that the area to be photographed does not include the coating layer is photographed. The samples are preferably of a uniform thickness. To prevent breakage of samples, the samples preferably have a thickness of at least 0.5 mm or more. Each sample may be photographed after cutting the porous composite into a size of 5.0-mm×5.0-mm. However, preferably, each sample having a dimension including a square range of 5.0-mm×5.0-mm is prepared and photographed with a SEM, and then a 5.0-mm×5.0-mm range can be designated on the photographed image.

Fractal Dimension (D)

Fractal dimension (D) is calculated by the following method. All the image processing steps shown below are performed by using an image processing software ImageJ (Ver. 1.48 or later).

(1) Capture an SEM image in which a square range of 5.0-mm×5.0-mm is designated (hereinafter referred to as "analysis image" in this paragraph) into ImageJ.
(2) Threshold the analysis image into a binary image (threshold value: 90 pixels).
(3) Reverse the color tones.
(4) Divide the analysis image into $n^2$ blocks (n=2, 3, 4, 5).
(5) For each block obtained by dividing the analysis image into $n^2$ blocks, calculate the area fraction of the area occupied by agglomerated particles of OCP to the entire area of the block.
(6) For the analysis image divided into $n^2$ blocks, calculate the average area fraction ($\mu_n$) of all the blocks and the standard deviation ($\delta_n$).
(7) Calculate D(n) by the following formula.

$$D(n)=\delta_n/\mu_n$$

(8) Plot D(n) and 1/n on a double logarithmic graph to obtain the slope of an approximation line (power approximation).
(9) Determine a fractal dimension (D) by multiplying the slope of the approximation line by −1.

Step (4) may be performed before step (2). Step (4) can be performed by an image processing software other than ImageJ, such as Windows Paint. When binarization in step (2) cannot be performed because of the color tones of the SEM image, or when the portions not occupied by agglomerated particles of OCP are confused with the portions occupied by agglomerated particles of OCP, only the portions containing the agglomerated particles of OCP can be first smeared with black and the other portions can be in white color, or only the portions occupied by agglomerated particles can be smeared with white and the other portions can be in black color. The image is then captured into ImageJ and subjected to step (2) and subsequent steps. When only the agglomerated particles of OCP are smeared with black and the other portions are in white color, step (3) of reversing the color tones is unnecessary.

Proportion of Agglomerated Particles of OCP

The porous composite of the present invention is such that in an image obtained by enlarging a 5.0-mm×5.0-mm range of a plane of the porous composite 15 times with a scanning electron microscope (SEM), the area fraction of the area occupied by agglomerated particles of OCP to the total area, set to 1, is preferably 0.05 or more but 0.40 or less, more preferably 0.10 or more but 0.30 or less, and even more preferably 0.15 or more but 0.25 or less. The area fraction of the agglomerated particles of OCP can be obtained from the area fraction of the area occupied by the agglomerated particles of OCP to the area of each block calculated in the process of calculating the fractal dimension (D).

Proportion of Agglomerated Particles of 300 μm or More

In the present invention, the area of the agglomerated particles of OCP having a length of 300 μm or more preferably accounts for 75% or more, more preferably 85% or more, and even more preferably 90% or more, of the total area of the agglomerated particles of OCP. The presence of relatively large agglomerated particles of 300 μm or more in a specific proportion or higher can continuously promote osteoconduction over a long period of time, and also plays an important role in reinforcing the strength of the skeletal structure of collagen of the porous composite. The total area of the agglomerated particles of OCP herein refers to the total of the areas occupied by all the visually detectable particles in the above SEM image. Having a length of 300 μm or more means that in the SEM image, the distance between a line tangent to the contour of an agglomerated particle and another tangent line drawn in parallel with the first tangent line so as to have the longest interval therebetween is 300 μm or more.

Specifically, the proportion of the agglomerated particles of 300 μm or more is calculated by the following method.

(1) Capture an SEM image in which a square range of 5.0-mm×5.0-mm is designated (hereinafter referred to as "analysis image" in this paragraph) into ImageJ.
(2) Threshold the analysis image into a binary image (threshold value: 90 pixels).
(3) Reverse the color tones.
(4) Determine the total area of agglomerated particles of OCP.
(5) Extract agglomerated particles of OCP having a length of 300 μm or more.
(6) Calculate the proportion of agglomerated particles of OCP having a length of 300 μm ($R_d$) from the total area of agglomerated particles of OCP ($S_w$) and the area of agglomerated particles of OCP having a length of 300 μm ($S_d$) according to the following formula.

$$R_d=S_d/S_w\times100$$

When binarization in (2) cannot be performed because of the color tones of the SEM image, or when the portions not occupied by agglomerated particles of OCP are confused with the portions occupied by agglomerated particles of OCP, only the portions occupied by agglomerated particles of OCP can be first smeared with black and the other portions are in white color, or only the portions occupied by agglomerated particles of OCP can be first smeared with white and the other portions can be in black color. The resulting image is then captured into ImageJ and subjected to step (2) and subsequent steps. When only the portions occupied by the agglomerated particles of OCP are smeared with black and the other portions are in white color, step (3) of reversing the color tones is unnecessary.

Area Percentage of the Portions Consisting of Collagen

The porous composite of the present invention is preferably such that in an image obtained by enlarging a 5.0-mm×5.0-mm range of a plane of the porous composite 15 times with a scanning electron microscope (SEM), the area of c) portions consisting of collagen accounts for 5% or less of the total area of a) portions consisting of agglomerated particles of octacalcium phosphate, b) portions consisting of octacalcium phosphate microparticles and collagen, and the c) portions consisting of collagen.

The porous composite according to a preferred embodiment of the present invention comprises a) portions consisting of agglomerated particles of OCP, b) portions consisting of OCP microparticles and collagen, and c) portions consisting, of collagen. Among these, a) portions consisting of agglomerated particles of OCP refer to portions in which calcium phosphate aggregates and particulates can be confirmed with the naked eye in a 15-fold enlarged SEM image of the porous composite. In the SEM image, the portions a) are usually represented in a color close to white. When the portions a) are subjected to elemental analysis, large amounts of calcium Ca and phosphorus P are detected. b) Portions consisting of OCP microparticles and collagen refer to portions in which fine OCP particles of less than 100 μm or the like are present in a sponge-like structure of collagen, and OCP microparticles are difficult to be confirmed with the naked eye in a 15-fold enlarged SEM image. In the SEM image, b) portions consisting of OCP microparticles and collagen are usually less bright than a) portions consisting of agglomerated particles of OCP and are represented in gray to white color. When the portions b) are subjected to elemental analysis, carbon C, calcium Ca, and phosphorus P are detected. c) Portions consisting of collagen refer to portions in which only a trace of or no OCP microparticles are present in a sponge-like structure of collagen. In the SEM image, c) portions consisting of collagen are represented in a dark color close to black. When the portions c) are subjected to elemental analysis, carbon C is detected and calcium Ca and phosphorus P are scarcely detected.

The area percentage of the portions consisting of collagen is determined by the following method.
(1) Capture an SEM image in which a square range of 5.0-mm×5.0-mm is designated (hereinafter referred to as "analysis image" in this paragraph) into ImageJ.
(2) Binarize the analysis image (threshold value: 90 pixels).
(3) Extract the portions consisting of collagen.
(4) Calculate the area of the collagen portions ($S_c$).
(5) Calculate the area of the analysis image ($S_A$).
(6) Calculate the area percentage of the portions consisting of collagen ($R_c$) by the following formula.

$$R_c = S_c/S_A \times 100$$

When binarization in step (2) cannot be performed because of the color tones of the SEM image, or when the portions consisting of collagen are confused with the portions other than the portions consisting of collagen, only the portions consisting of collagen can be first smeared with black and the other portions can be in white color, or only the portions consisting of collagen can be smeared with white and the other portions can be in black color. The resulting image is then captured into ImageJ and subjected to step (2) and subsequent steps. When the portions consisting of collagen are smeared with white and the other portions are in black color, the step of reversing the color tones is necessary between processes (2) and (3).

The area percentage of the portions consisting of collagen is preferably 5% or less, more preferably 4% or less, and even more preferably 3% or less, based on the total area of the analysis image. When the portions consisting of collagen account for more than 5%, the porous composite has a non-uniform structure and may have reduced osteoconduction. Further, when the portions consisting of collagen account for more than 5%, the compressive modulus is significantly reduced.

One embodiment of the present invention is a porous composite such that in an image obtained by enlarging a 5.0-mm×5.0-mm range of a plane of the porous composite 15 times with a scanning electron microscope (SEM),
agglomerated particles of OCP have a fractal dimension (D) of 0.70 or more; and
the image includes a) portions consisting of agglomerated particles of octacalcium phosphate, b) portions consisting of octacalcium phosphate microparticles and collagen, and c) portions consisting of collagen, arid the area of c) the portions consisting of collagen accounts for 5% or less of the image.

Another embodiment of the present invention is a porous composite such that in an image obtained by enlarging a 5.0-mm×5.0-mm range of a plane of the porous composite 15 times with a scanning electron microscope (SEM),
agglomerated particles of OCP have a fractal dimension (D) of 0.60 or more;
the area of agglomerated particles having a length of 300 μm or more accounts for 75% or more of the total area of the agglomerated particles of OCP; and
the area of c) portions consisting of collagen accounts for 5% or less of the total area of a) portions consisting of agglomerated particles of octacalcium phosphate, b) portions consisting of octacalcium phosphate microparticles and collagen, and the c) portions consisting of collagen.

More preferably, the fractal dimension (D) is 0.70 or more and the area of agglomerated particles having a length of 300 μm or more accounts for 85% or more. Even more preferably, the fractal dimension (D) is 0.80 or more and the area of agglomerated particles having a length of 300 μm or more accounts for 90% or more.

Compressive Modulus

The porous composite preferably has a compressive modulus of 0.05 MPa or more, more preferably 0.08 MPa to 0.30 MPa, and even more preferably 0.10 MPa to 0.20 MPa. When the compressive strength is less than 0.05 MPa, the workability of the porous composite tends to be reduced. In other words, when a bone defect site is filled with the porous composite of the present invention, a collapse of the porous composite or a crushing of pores, if it occurred, would adversely affect the subsequent bone regeneration. Although the upper limit of the compressive modulus is not particularly specified, it is preferably 0.30 MPa or less in terms of operating ease in filling a bone defect site.

The compressive modulus in the present invention is measured by the following method.

A cylindrical sample having a diameter of 8.5 mm and a length of 15 mm is immersed in a phosphate buffered saline (10 mM sodium phosphate, 0.14 M sodium chloride, pH 7.4) at a temperature of 25° C. and a humidity of 65% for 30 minutes. The water on the surface of the sample is then lightly blotted. A uniaxial load is applied to the sample using a precision universal tester (Autograph AGS-J, produced by Shimadzu Corporation, load cell capacity: 1 kN). Specifically, after a sample is set in such a manner that the long side of the sample is perpendicular to a lower platen (material: stainless steel, inner diameter: 100 mm, thickness: 25 mm), an upper platen (material: stainless steel, inner diameter: 100 mm, thickness: 25 mm) is lowered at a rate of 10 mm/min.

When the sample is deformed by 80%, the tester is stopped. The compressive modulus is calculated from the slope of the initial linear portion of the obtained stress-strain curve.

The porous composite of the present invention preferably has a pore size of 3 µm to 40 µm. If the pore size is more than 40 µm, the strength of the porous composite tends to be reduced. On the other hand, if the pore size is less than 3 µm, it is difficult for bone metabolic cells, such as osteoblasts, to migrate into the porous composite, and the effect of promoting bone regeneration may be reduced. The porous composite of the present invention more preferably has a pore size of 5 µm to 20 µm.

The pore size is measured by pore distribution measurement using a mercury porosimeter. Specifically, it is measured by the following method.

Measurement of Pore Size

As a pretreatment, samples are dried at a constant temperature of 120° C. for 4 hours. For each of the samples after the pretreatment, the pore distribution of pores having a diameter of 0.0018 µm to 200 µm is determined under the following conditions by the mercury intrusion method using the following measurement device.

Measurement device: AutoPore IV 9520 (produced by Micromeritics)

Measurement conditions:
  contact angle between mercury and sample: 140°
  Surface tension of mercury: 0.48 N/m (converted by 1 dyne=$10^{-5}$N)

The pore size in the present invention refers to a value of micropore size showing the maximum value of the peak having the largest area in the pore distribution curve obtained from the measured pressure by the mercury intrusion method.

The porosity (void ratio) of the porous composite is preferably 80% to 99%, and more preferably 85% to 98%. The porosity is determined by the following formula from the total pore volume measured by the mercury intrusion method and apparent density.

Porosity (%) =Total pore volume/{(1/Apparent density)+Total pore volume}×100

The shape of the porous composite of the present invention is preferably a rectangular parallelepiped (block body), a cylinder, a tablet, or a granule. When the porous composite is a rectangular parallelepiped, the porous composite preferably has a size of greater than or equal to 5 mm×5 mm×5 mm. In general, the upper limit is preferably in the range of 100 mm×100 mm×100 mm. The rectangular parallelepiped is not limited to a cube. When the porous composite is cylindrical, the porous composite preferably has a diameter of 5 mm to 50 mm and a height in the range of 1 mm to 50 mm. When the porous composite is granular, the shape of the granule is not limited to spheres, and may be indefinite; however, the porous composite preferably has a diameter of 0.1 mm to 10 mm.

The porous composite of the present, invention is used by filling a bone defect site with the porous composite. When sufficient blood or body fluid is present at the bone defect site, the bone defect site can be filled with the porous composite as is, or after the porous composite is cut into an appropriate shape. When sufficient blood or the like is not present at the bone defect site, or when the porous composite cannot be used in its original form to fill the bone defect site therewith, the bone defect site can be filled with the porous composite after the porous composite is immersed in blood, physiological saline, or the like and the porous composite is confirmed to have sponge-like elasticity.

Method for Producing Porous Composite

The method for producing the porous composite of the present invention is preferably a production method comprising mixing OCP with collagen. For example, the following production method can be used.

(1) First, OCP is added to a solution of gelled collagen having a concentration of 0.1 wt. % to 5 wt. % and a pH of 7 to 8, and kneaded to prepare a mixture of OCP and collagen. (2) Subsequently, the mixture is molded in a suitable mold, frozen, and freeze-dried to obtain a composite. (3) The obtained composite is optionally subjected to heat dehydration crosslinking treatment, and further sterilized by a conventional sterilization method (e.g., γ-ray irradiation, electron beam irradiation, or ethylene oxide gas).

It was common technical knowledge of persons skilled in the art that full kneading is necessary in the step of kneading collagen and OCP. Surprisingly, however, the present inventors found that full kneading reduces the fractal dimension or the proportion of particles of 300 µm or more. In the kneading step, stirrers with impellers, such as propeller-type stirrers with 2 blades to 4 blades or paddle-type stirrers, or rotating/revolving mixers can be used. When a stirrer with an impeller is used, stirring is preferably performed at 100 rpm to 300 rpm for 15 seconds to 300 seconds, and more preferably at 100 rpm to 300 rpm for 30 seconds to 120 seconds. When a rotating/revolving mixer is used, stirring is preferably performed at 500 rpm to 1500 rpm for 30 seconds to 300 seconds, and more preferably at 500 rpm to 1500 rpm for 45 seconds to 120 seconds. The step of kneading collagen and OCP can also be manually performed by using a spatula or the like. In this case as well, the stirring is preferably performed at a constant rate for 30 seconds to 120 seconds. Preferably, the stirring time is appropriately adjusted according to the rotational speed.

The method for producing the porous composite of the present invention preferably comprises a step of freeze-drying after a gel, sol, or liquid containing OCP and collagen is rapidly frozen by immersion in a liquid refrigerant. The liquid refrigerant is a liquid having a temperature lower than the freezing temperature of the gel, sol, or liquid containing OCP and collagen. Examples of such liquids include methanol, ethanol, acetone, acetonitrile, and liquid nitrogen. The temperature of the liquid refrigerant is preferably −20° C. or less, more preferably −40° C. or less, and still more preferably −80° C. or less.

Rapidly freezing the gel, sol, or liquid containing octacalcium phosphate and collagen by immersion in a liquid refrigerant is considered to reduce the pore size of the resulting porous composite.

The porous composite of the present invention is preferably subjected to heat treatment or dehydrothermal crosslinking treatment. The heat treatment leads to a collapse of a part of the OCP molecular structure, thus facilitating the migration of osteogenic cells and promoting bone regeneration, while allowing collagen to crosslink to enhance shape retention.

The temperature of the heat treatment is preferably 50° C. to 200° C., and more preferably 60° C. to 180° C. The heat treatment is preferably performed under reduced pressure. The pressure is preferably 0 Pa to 3000 Pa, and more preferably 0 Pa to 300 Pa. The treatment time of the heat treatment is preferably 2 hours to 10 days, and more preferably 12 hours to 5 days.

The porous composite of the present invention may contain, in addition to OCP and collagen, for example, cytokine (e.g., bone morphogenetic protein-2, transforming growth factor β1, etc.) having a bone-forming ability. Containing such cytokine can increase the bone regeneration speed.

The porous composite of the present invention may further contain other components that are commonly used in this field. Examples of such components include bioabsorbable polymers (e.g., polyglycolic acid, polylactic acid, polylactic acid-polyethylene glycol copolymer, etc.), bioabsorbable calcium phosphates other than OCP (e.g., β-TCP), and non-resorbable calcium phosphates (e.g., hydroxyapatite).

Bone Regeneration Material

The present invention further relates to a bone regeneration material containing the porous composite. The bone regeneration material can be used, for example, for bone defect repair in the dental oral surgery field and orthopedic surgery field, and bone defect repair after craniotomy or thoracotomy. For example, in the dental oral surgery field, when a bone defect caused by periodontal disease, a cystic cavity, an atrophic alveolar ridge, a cleft jaw, a tooth-extraction cavity, or the like is filled with a bone regeneration material comprising the porous composite, an excellent bone regeneration effect can be confirmed after several weeks, to several months. In the orthopedic surgery field, for example, in the case of a bone defect after resection of a bone tumor or a bone defect caused by trauma, such as a bone fracture, the bone defect site can be filled with the bone regeneration material of the present invention to thereby promote bone regeneration.

EXAMPLES

The present invention is described in more detail below with reference to Examples. However, the present invention is not limited thereto.

Example 1

(1) Preparation of OCP

First, liquid 1 and liquid 2 for preparation of OCP were prepared in the following manner.

Liquid 1: Sodium dihydrogen phosphate dihydrate (31.2 g) was dissolved in 2500 g of distilled water to prepare liquid 1.

Liquid 2: Calcium acetate monohydrate (35.2 g) was dissolved in 2500 g of distilled water to prepare liquid 2.

Subsequently, liquid 1 was placed in a separable flask, and heated to 70° C. using a mantle heater. Next, while liquid 1 was stirred at a rate of 250 rpm using a stirrer (MAZELA Z, produced by Tokyo Rikakikai Co., Ltd.) equipped with stirring blades (blade diameter: 12 cm), liquid 2 was added dropwise to liquid 1 at a rate of about 28 mL/min. After completion of the dropwise addition, the mixture of liquid 1 and liquid 2 was further stirred at 70° C. at 250 rpm for 2 hours.

Subsequently, the precipitate produced in the above mixture was filtered through a membrane filter (pore size: 3 μm; A300A293C, produced by Advantec Toyo Kaisha, Ltd.) and collected. The collected precipitate was dispersed in 1500 mL of distilled water and washed by stirring for 15 minutes. Such filtering and washing steps were further repeated 3 times.

Subsequently, the washed precipitate was dried in a constant temperature dryer at 30° C. for 24 hours. The dried precipitate was ground with an electric mill and then classified to a particle size of 300 μm to 500 μm using sieves, thus obtaining a powder. Finally, the obtained powder was subjected to dry-heat sterilization at 120° C. for 2 hours.

(2) Preparation of OCP/Collagen Composite (Porous Composite)

One part by weight of pig dermis-derived collagen comprising type-I collagen and type-III collagen (NMP Collagen PS, produced by NH Foods Ltd.) was dissolved in 200 parts by weight of distilled water cooled to 4° C., thus obtaining a collagen solution in a concentration of about 0.5 wt. %. While the solution temperature was maintained at 4° C., an aqueous sodium hydroxide solution was added to the collagen aqueous solution, and the pH was adjusted to about 7.4 to obtain a collagen suspension. Subsequently, the collagen suspension was placed in a centrifuge bottle and centrifuged by a centrifugal separator (GRX-250, produced by Tomy Seiko Co., Ltd.) at a centrifugal force of 7,000×g for 20 minutes. The supernatant was removed so that the resulting collagen suspension contained collagen in an amount of 3 wt. %, thus obtaining a collagen gel.

Subsequently, after OCP (particle size: 300 μm to 500 μm) was added to the collagen gel in such an amount that the weight ratio of OCP to collagen was 77:23, the mixture was stirred at a rotational speed of 300 rpm for 60 seconds using a stirrer (MAZELA Z, produced by Tokyo Rikakikai Co., Ltd.) equipped with stirring blades (produced by Sogo Laboratory Glass Works Co., Ltd., 4 blades, blade diameter: 7 cm) to obtain an OCP/collagen composite gel. The gel was placed in a plastic container having a cylindrical inner space (inner diameter: 8.5 mm, volume: about 3.0 cm$^3$) and centrifuged at a centrifugal force of 230×g for 1 minute and defoamed.

The container was hermetically sealed and rapidly frozen by dipping in a large excess of −80° C.-cooled methanol relative to the volume of the product to be frozen. After opening the container, the frozen product was dried by a lyophilizer (−10° C., 48 hours) and molded. The molded product was then heated at 150° C. under reduced pressure for 24 hours for dehydrothermal crosslinking. The obtained cylindrical product was cut to a thickness of 1.5 mm or 15 mm with a surgical knife and finally irradiated with electron beams (15 kGy) for sterilization. A porous composite of Example 1 was thus obtained.

Example 2

A porous composite was obtained in Example 2 in the same manner as in Example 1 except that a collagen gel and OCP were mixed at a rotational speed of 300 rpm for 300 seconds using a stirrer with blades.

Example 3

A porous composite was obtained in Example 3 in the same manner as in Example 1 except that a collagen gel and OCP were mixed at a rotational speed of 1000 rpm for 60 seconds using a rotating/revolving mixer (Awatori Rentaro ARE-310, produced by Thinky Corporation).

Comparative Example 1

A porous composite was obtained in Comparative Example 1 in the same manner as in Example 1 except that a collagen gel and OCP were mixed at a rotational speed of 100 rpm for 15 seconds using a stirrer with blades.

Comparative Example 2

A porous composite was obtained in Comparative Example 2 in the same manner as in Example 1 except that a collagen gel and OCP were mixed at a rotational speed of 300 rpm for 900 seconds using a stirrer with blades.

Comparative Example 3

A porous composite was obtained in Comparative Example 3 in the same manner as in Example 1 except that a collagen gel and OCP were mixed at a rotational speed of 300 rpm for 15 seconds using a rotating/revolving mixer.

Comparative Example 4

A porous composite was obtained in Comparative Example 4 in the same manner as in Example 1 except that a collagen gel and OCP were mixed at a rotational speed of 2000 rpm for 900 seconds using a rotating/revolving mixer.

Image Analysis

Image analysis was performed on SEM images by observing a cross-section of each sample prepared by cutting to a thickness of 1.5 mm, under the following conditions. The analysis range was inside of an about 5-mm-square area freely-selected from the cross-section of the sample (hereinafter referred to as analysis image), which was used for analysis.

Measuring apparatus: SU151G, produced by Hitachi Ltd.
Measurement conditions: accelerating voltage 15-kV low vacuum (30 Pa)
Reflection electron microscopic observation
WD: 40 mm
Magnification: ×15

Fractal Dimension

The fractal dimension (D) was used to quantify the degree of dispersion of OCP particles on a collagen matrix. The fractal dimension (D) was calculated by the following procedure: All the image processing steps shown below were performed using ImageJ image processing software.
1. Capture an analysis image.
2. Binarize the analysis image (threshold: 90 pixels).
3. Reverse the color tones.
4. Divide the analysis image into $n^2$ blocks (n=2, 3, 4, 5).
5. For each block, calculate the area fraction of the image representing OCP particles.
6. At each division level, calculate the area fraction average ($\mu_n$) and standard deviation ($\delta_n$).
7. Calculate D(n) by the following formula:

$$D(n)=\delta_n/\mu_n$$

8. Plot D (n) and 1/n on a double logarithmic graph to obtain the slope of an approximation line.
9. Multiply the slope of the approximation line by −1 to obtain a fractal dimension (D).

Proportion of OCP Particles of 300 μm or More

The proportion of the OCP particles of 300 μm or more is calculated by the following procedure:
1. Capture an analysis image.
2. Binarize the analysis image (threshold: 90 pixels).
3. Reverse the color tones.
4. Determine the particle size.
5. Extract OCP particles of 300 μm or more.
6. Calculate the total particle area ($S_w$) and the area of OCP particles of 300 μm or more ($S_d$).
7. Calculate the proportion of OCP particles of 300 μm or more ($R_d$) by the following formula:

$$R_d=S_d/S_w\times100$$

The particle size in this measurement is defined as the distance between a line tangent to the contour of an agglomerated particle and another tangent line drawn in parallel with the first tangent line so as to have the longest interval therebetween, which is 300 μm or more.

Proportion of Collagen Portions

As an index to assess whether OCP and collagen gel have been sufficiently mixed, the proportion of collagen portions is calculated from the analysis image. The proportion of collagen portions was calculated by the following procedure:
1. Capture an analysis image.
2. Binarize the analysis image (threshold: 90 pixels).
3. Extract collagen portions.
4. Calculate the area of the collagen portions ($S_c$).
5. Calculate the area of the analysis image ($S_A$).
6. Calculate the area percentage of the collagen portions ($R_c$) by the following formula:

$$R_c=S_c/S_A\times100$$

Compressive-modulus Measurement

A cylindrical sample having a diameter of 8.5 mm and a height of 15 mm was immersed in a phosphate buffered saline (10 mM sodium phosphate, 0.14 M sodium chloride, pH 7.4) at a temperature of 25° C. and a humidity of 65% for 30 minutes. The water on the surface of the sample was then lightly blotted. A uniaxial load was applied to the sample using a precision universal tester (Autograph AGS-J, produced by Shimadzu Corporation, load cell capacity: 1 kN). Specifically, after a sample was set in such a manner that the long side of the sample was perpendicular to a lower platen (material: stainless steel, inner diameter: 100 mm, thickness: 25 mm), an upper platen (material: stainless steel, inner diameter: 100 mm, and thickness: 25 mm) was lowered at a rate of 10 mm/min. When the sample was deformed by 80%, the tester was stopped. The compressive modulus was calculated from the slope of the initial linear portion of the obtained stress-strain curve.

Porosity Measurement

For each of the cylindrical (tablet-shaped) samples having a diameter of 8.5 mm and a thickness of 1.5 mm obtained in Examples 1 to 3 and Comparative Examples 1 to 4, the porosity was measured in the following manner.

As a pretreatment, samples were dried at a constant temperature of 120° C. for 4 hours. For each sample after the pretreatment, pore distribution of pores having a pore diameter of 0.0036 μm to 200 μm was determined under the following conditions by the mercury intrusion method using the following measurement device.

Measurement device: AutoPore IV9520 (available from Micromeritics Japan)
Measuring conditions:
  Contact angle between sample and mercury: 140°
  Surface tension of mercury: 0.48 N/m (converted by 1 dyne $=10^{-5}$N)

The porosity is determined by the following formula using the total pore volume and apparent density measured by the mercury intrusion method:

Porosity (%)=total pore volume/{(1/apparent density)+total pore volume}×100

Table 1 shows the measurement results of the fractal dimension (D), proportion of OCP particles of 300 μm or more, proportion of collagen portions, porosity, and compressive modulus.

TABLE 1

| | Mixing method | Stirring rate | Time | Fractal dimension | Proportion of particles of 300 μm or more (%) | Proportion of collagen portions (%) | Porosity (%) | Compressive modules (MPa) |
|---|---|---|---|---|---|---|---|---|
| Comparative Example 1 | Stirrer, 4 blades | 100 rpm | 15 seconds | 0.78 | 96.3 | 11.6 | 95 | 0.064 |
| Example 1 | Stirrer, 4 blades | 300 rpm | 60 seconds | 0.80 | 93.1 | 2.6 | 97 | 0.107 |
| Example 2 | Stirrer, 4 blades | 300 rpm | 300 seconds | 1.19 | 88.8 | 0 | 96 | 0.105 |
| Comparative Example 2 | Stirrer, 4 blades | 300 rpm | 900 seconds | 0.56 | 88.2 | 0 | 97 | 0.045 |
| Comparative Example 3 | Rotating/revolving mixer | 300 rpm | 15 seconds | 0.53 | 90.1 | 45.2 | 97 | 0.034 |
| Example 3 | Rotating/revolving mixer | 1000 rpm | 60 seconds | 0.97 | 91.6 | 0 | 98 | 0.101 |
| Comparative Example 4 | Rotating/revolving mixer | 2000 rpm | 900 seconds | 0.68 | 74.0 | 0 | 97 | 0.058 |

The results in Table 1 show the following.

All the samples (porous composites) obtained in Examples 1 to 3 had a fractal dimension of 0.70 or more. The proportion of particles of 300 μm or more was 75% or more. The proportion of collagen portions was 3% or less. OCP particles were uniformly dispersed while the predetermined particle size was maintained. Sufficient mixing was achieved.

The sample obtained in Comparative Example 1 had a fractal dimension of 0.78. The proportion of particles of 300 μm or more was 96%. OCP particles were uniformly dispersed while the predetermined particle size was maintained. However, due to slightly insufficient stirring, the proportion of collagen portions was 11% and sufficient mixing was not achieved.

The sample obtained in Comparative Example 2 was such that the proportion of particles of 300 μm or more was 88% and no portion consisting only of collagen existed. Sufficient mixing was achieved while the predetermined particle size was maintained. Surprisingly, however, excessive stirring resulted in disproportional presence of OCP particles in the peripheral portion of the disk, and the sample of Comparative Example 2 had a low fractal dimension of 0.56 or less.

The sample obtained in Comparative Example 3 was such that the proportion of particles of 300 μm or more was 90% and the predetermined particle size was maintained. However, the fractal dimension was as low as 0.53 and the collagen portions accounted for 45%, which is a very high proportion. These results suggest that clearly insufficient stirring resulted under such stirring conditions.

The sample obtained in Comparative Example 4 had a fractal dimension of 0.68 and no portion consisting only of collagen existed. Although uniform dispersion of OCP particles and sufficient mixing were observed, the proportion of the particles of 300 μm or more was 74% and maintaining the predetermined particle size was difficult. This is presumably because OCP particles were disintegrated by long-term vigorous stirring and the proportion of the particles of 300 μm or more decreased.

The samples obtained in Examples 1 to 3 had a compressive modulus of about 0.1 MPa, which is 1.6 to 3.1 times as high as the compressive modulus of the samples obtained in Comparative Examples 1 to 4. This is presumably because in Examples 1 to 3, OCP particles were uniformly dispersed in the entire composite and there was only a small portion in which OCP and collagen were insufficiently mixed and OCP thus functioned efficiently as a reinforcer.

Porous Composite Implantation Test

Male SD rats (12 weeks old) were used as test animals. The rats were intraperitoneally anesthetized, and skin and periosteal incisions were made in the calvarium region of each rat to expose the calvarium. A standardized full-thickness bone defect (diameter: about 9 mm), for which spontaneous recovery could not be expected, was created in each rat. One of the disc-shaped porous composites produced in Example 1, Example 2, Comparative Example 3, and Comparative Example 4 was implanted into the bone defect of each rat. One rat each was used for the test of implanting the porous composites produced in Examples 1 and 2 and Comparative Example 4, whereas two rats were used in the test of implanting the porous composite produced in Comparative Example 3. After each sample was implanted, the periosteum and skin were sutured and the surgery was completed. The observation period after surgery was 10 weeks for each group.

Ten weeks after surgery, the rats were sacrificed with an overdose of pentobarbital anesthesia. The calvarium and surrounding tissues were collected and fixed by immersion in 0.1 M phosphate-buffered 4% paraformaldehyde (pH 7.4). After the calvarium and surrounding tissues were decalcified with 10% EDTA and paraffin samples were prepared, tissue slices with a thickness of 6 μm were prepared by cutting in the frontal plane and stained with hematoxylin-eosin (HE) to prepare tissue samples.

FIGS. 6 to 10 show the results of each group. In Examples 1 and 2, uniform dispersion of the agglomerated particles of OCP can be confirmed. In the specimen into which the porous composite of Example 1 was implanted, new bone was observed in many portions within the bone defect region and the other portions were also observed to be occupied with connective tissue associated with bone regeneration. In the sample into which the porous composite of Example 2 was implanted, many portions within the entire bone defect portion were occupied with new bone. In particular, on the defect periphery, the boundary between the defect portion and the bone bed is blurred and active bone regeneration is exhibited. In any of the samples, as bone regeneration progresses, the size of agglomerated particles of OCP become smaller. Further, migration of new bone tissue into the agglomerated particles of OCP can also be observed. The results suggest that OCP exerts sustained effects and effectively acts during the period.

Figure 1:
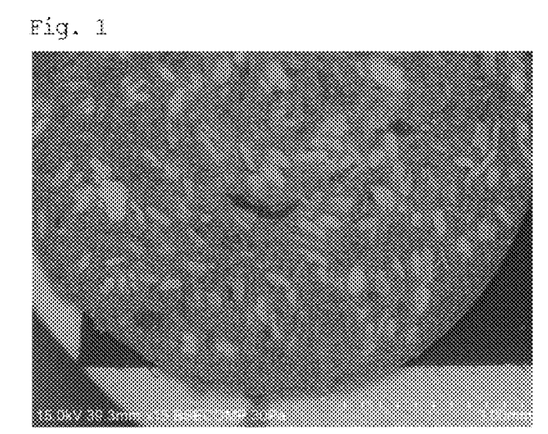
FIG. 1 is an SEM observation image of the porous composite obtained in Example 1.
Figure 2:
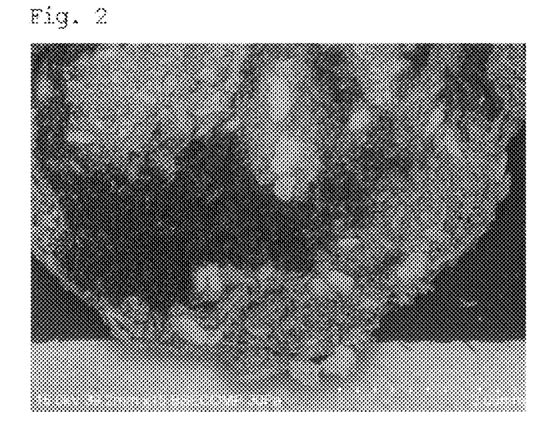
FIG. 2 is an SEM observation image of the porous composite obtained in Comparative Example 3.
Figure 3:
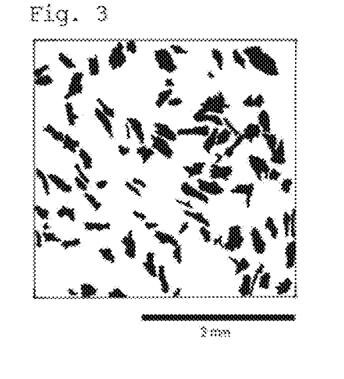
FIG. 3 is an analysis image used to calculate the fractal dimension and the proportion of particles in Example 1.
Figure 4:
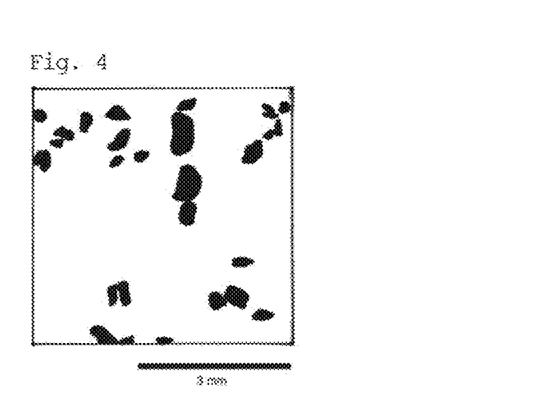
FIG. 4 is an analysis image used to calculate the fractal dimension and the proportion of particles in Comparative Example 3.
Figure 5:
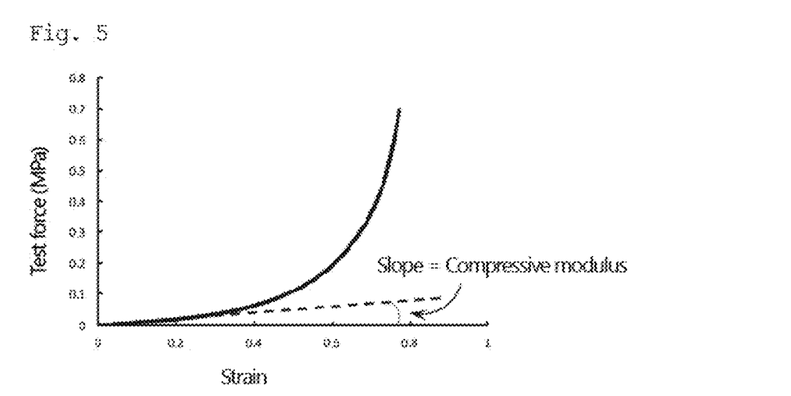
FIG. 5 is a graph showing a stress-strain curve obtained by measuring the compressive modulus of the porous composite obtained in Example 1.
Figure 6:
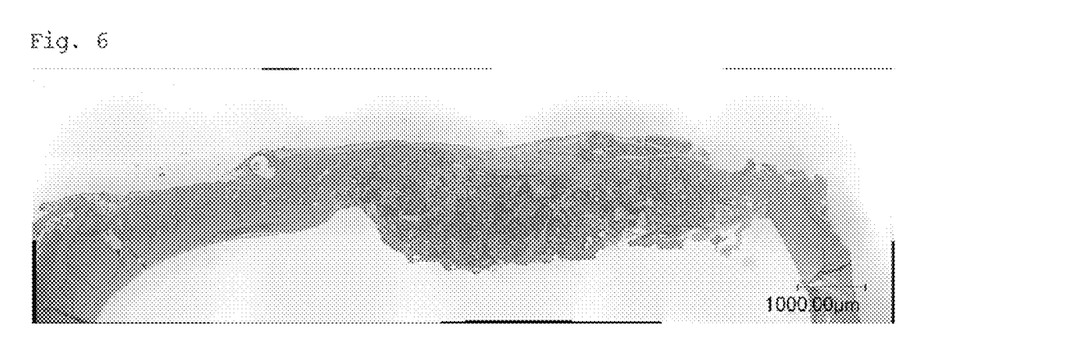
FIG. 6 is an illustration of a stained histological specimen of a bone defect site treated with the porous composite obtained in Example 1. The upper side is the skin side, and the lower side is the dura mater side.
Figure 7:
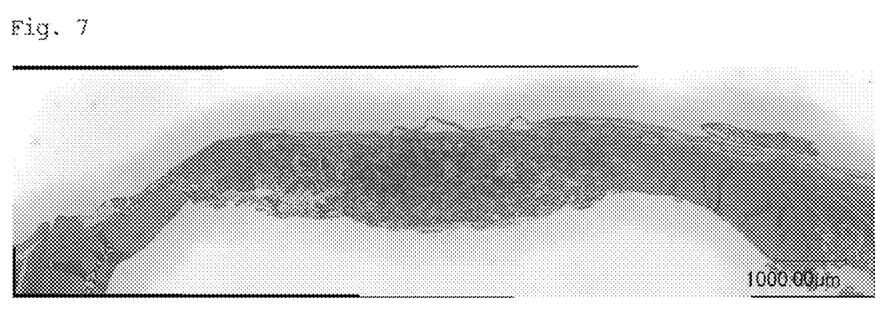
FIG. 7 is an illustration of a stained histological specimen of a bone defect site treated with the porous composite obtained in Example 2. The upper side is the skin side, whereas the lower side is the dura mater side.
Figure 8:
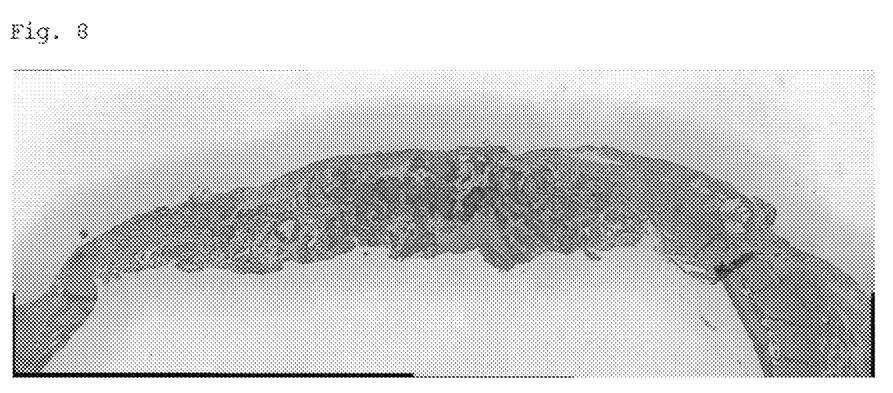
FIG. 8 is an illustration of a stained histological specimen of a bone defect site treated with the porous composite obtained in Comparative Example 3. The upper side is the skin side, whereas the lower side is the dura mater side.
Figure 9:
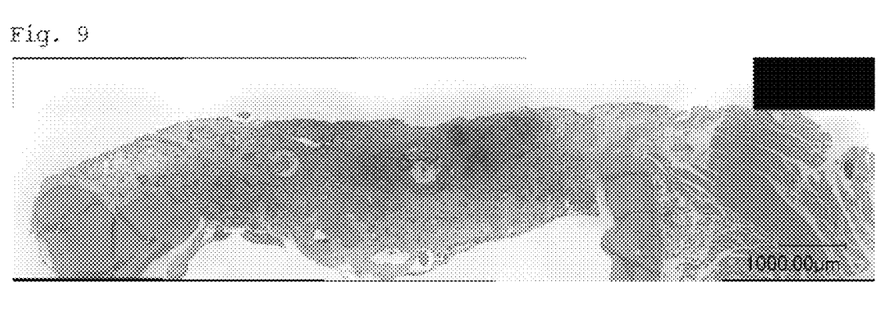
FIG. 9 is an illustration of a stained histological specimen of a bone defect site treated with the porous composite obtained in Comparative Example 3. The upper side is the skin side, whereas the lower side is the dura mater side.
Figure 10:
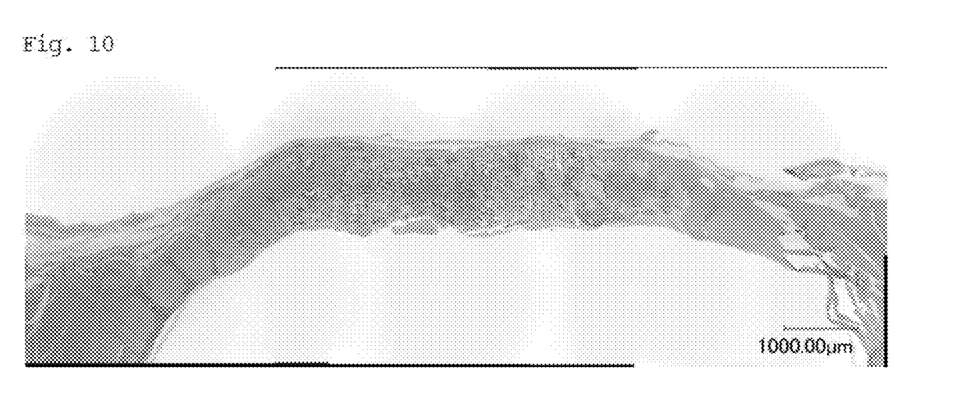
FIG. 10 is an illustration of a stained histological specimen of a bone defect site treated with the porous composite obtained in Comparative Example 4. The upper side is the skin side, whereas the lower side is the dura mater side.

In contrast, in the two samples prepared using the porous composite of Comparative Example 3, agglomerated particles of OCP were unevenly distributed or scarcely present. In the tissue sample shown in FIG. 8, new bone is partially observed. However, new bone formation over the entire bone defect is not noticeable. Further, the agglomerated particles of OCP remained almost the same in size, and migration of new bone tissue into the agglomerate particles is also not observed. In the tissue sample shown in FIG. 9, no new bone is clearly observed, and the material derived from collagen remains undegraded. The results shown in FIGS. 8 and 9 both suggest that bone regeneration was not so active in Comparative Example 3. In the sample into which the porous composite of Comparative Example 4 was implanted, agglomerated particles of OCP were sparsely present, and very little new bone formation was observed. Further, the sponge structure derived from collagen was observed to remain in the sample. These results suggest that cell migration required for bone regeneration hardly progressed.

INDUSTRIAL APPLICABILITY

The porous composite of the present invention and the bone regeneration material comprising the porous composite has high bone regeneration capacity and appropriate mechanical strength. Therefore, the bone regeneration material is useful mainly for bone defect repair in the dental oral surgery field and orthopedic surgery field.

The invention claimed is:
1. A porous composite comprising:
octacalcium phosphate, and
collagen,
wherein the octacalcium phosphate is provided as (i) agglomerated particles of octacalcium phosphate having a size greater than 100 μm and having a fractal dimension of 0.70 or more as measured by a scanning electron microscope, and (ii) octacalcium phosphate microparticles having a size of less than 100 μm; and
wherein a collagen matrix without the octacalcium phosphate accounts for 5% or less of the total structure of the porous composite.
2. A porous composite comprising:
octacalcium phosphate, and
collagen,
wherein the octacalcium phosphate is provided as (i) agglomerated particles of octacalcium phosphate having a size greater than 100 μm and having a fractal dimension of 0.60 or more as measured by a scanning electron microscope, and (ii) octacalcium phosphate microparticles having a size of less than 100 μm; and
wherein agglomerated particles of octacalcium phosphate having a size of 300 μm or more account for 75% or more of the agglomerated particles of octacalcium phosphate having a size greater than 100 μm and having the fractal dimension of 0.60 or more as measured by the scanning electron microscope; and
wherein a collagen matrix without the octacalcium phosphate accounts for 5% or less of the total structure of the porous composite.
3. The porous composite according to claim 1, wherein the porous composite has a compressive modulus of 0.08 MPa or more.
4. A bone regeneration material comprising the porous composite according to claim 1.
5. The porous composite according to claim 2, wherein the porous composite has a compressive modulus of 0.08 MPa or more.
6. A bone regeneration material comprising the porous composite according to claim 2.
7. A bone regeneration material comprising the porous composite according to claim 3.
8. A bone regeneration material comprising the porous composite according to claim 5.

* * * * *